United States Patent
Ramachandran et al.

(10) Patent No.: US 8,325,334 B2
(45) Date of Patent: Dec. 4, 2012

(54) SUBSTRATE EDGE INSPECTION

(75) Inventors: Mahendra P. Ramachandran, Palo Alto, CA (US); Steven W. Meeks, Palo Alto, CA (US); Alireza S. Moghadam, San Jose, CA (US); Hung P. Nguyen, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 363 days.

(21) Appl. No.: 12/858,669

(22) Filed: Aug. 18, 2010

(65) Prior Publication Data

US 2011/0058174 A1 Mar. 10, 2011

Related U.S. Application Data

(60) Provisional application No. 61/240,560, filed on Sep. 8, 2009.

(51) Int. Cl.
*G01N 21/00* (2006.01)
*G01N 21/55* (2006.01)

(52) U.S. Cl. ............... 356/237.1; 356/445; 356/237.2; 356/237.4; 356/237.5

(58) Field of Classification Search .......... 356/445–448, 356/450–458
See application file for complete search history.

(56) References Cited

U.S. PATENT DOCUMENTS

| | | | |
|---|---|---|---|
| 6,943,897 B1 * | 9/2005 | Stenton et al. | 356/515 |
| 7,161,667 B2 * | 1/2007 | Meeks et al. | 356/237.2 |
| 7,161,668 B2 | 1/2007 | Meeks et al. | |
| 7,161,669 B2 * | 1/2007 | Velidandla et al. | 356/237.2 |
| 7,532,318 B2 * | 5/2009 | Meeks et al. | 356/237.2 |
| 7,656,519 B2 * | 2/2010 | Meeks et al. | 356/237.2 |
| 2006/0250609 A1 | 11/2006 | Meeks et al. | |
| 2006/0250610 A1 | 11/2006 | Meeks et al. | |
| 2006/0250611 A1 | 11/2006 | Velidandla et al. | |

* cited by examiner

*Primary Examiner* — Gregory J Toatley
*Assistant Examiner* — Jarreas C Underwood
(74) *Attorney, Agent, or Firm* — Luedeka Neely Group, P.C.

(57) ABSTRACT

An apparatus for inspecting an edge of a substrate. A light source produces a light beam, and a two-dimensional beam deflector receives the light beam and creates a semi-annular scanning beam. A first flared parabolic surface receives the semi-annular scanning beam and directs the semi-annular scanning beam onto the edge of the substrate, thereby creating specularly reflected light from the edge of the substrate. A second flared parabolic surface receives and directs the specularly reflected light to a detector. The detector receives the directed specularly reflected light and produces signals. An analyzer analyzes the signals and detects defects at the edge of the substrate.

20 Claims, 7 Drawing Sheets

SUBSTRATE EDGE INSPECTION

This application claims all rights and priority on prior pending U.S. provisional patent application Ser. No. 61/240,560 filed Sep. 8, 2009. This invention relates to the field of integrated circuit fabrication. More particularly, this invention relates to optical inspection of the substrates on which integrated circuits are formed.

FIELD

Introduction

Integrated circuits are often formed on monolithic or composite substrates, typically of a semiconducting material. As the term is used herein, "integrated circuit" includes devices such as those formed on monolithic semiconducting substrates, such as those formed of group IV materials like silicon or germanium or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

As engineers search for ways to reduce the cost of such integrated circuits, they have pushed for ways to extend the usable surface area of the substrate closer and closer to the edges of the substrate. This requires that the edges of the substrate be inspected to determine their fitness for forming usable circuits. However, most substrate edges are rounded, rather than perfectly square, which makes them difficult to inspect.

Some inspection equipment physically rotate an inspection light source and an inspection sensor around the edge of the substrate to capture the scan data. However, physically rotating an inspection head is a relatively time consuming process.

What is needed, therefore, is a system for reducing problems such as those described above, at least in part.

SUMMARY OF THE CLAIMS

The above and other needs are met by an apparatus for inspecting an edge of a substrate. A light source produces a light beam, and a two-dimensional beam deflector, such as an acousto-optic beam deflector, receives the light beam and creates a semi-annular scanning beam. A first flared parabolic surface receives the semi-annular scanning beam and directs the semi-annular scanning beam onto the edge of the substrate, thereby creating specularly reflected light from the edge of the substrate. A second flared parabolic surface receives and directs the specularly reflected light to a detector. The detector receives the directed specularly reflected light and produces signals. An analyzer analyzes the signals and detects defects at the edge of the substrate.

In this manner, entire radial portion of the edge of the substrate (from front to back) is inspected without moving either the substrate or the inspection optics, and as only the substrate is rotated, the entire peripheral edge of the substrate can be inspected in a single rotation of the substrate, again without any movement of the inspection head. Because the inspection head does not need to be repositioned during several different rotations of the substrate, the substrate can be inspected much faster than with prior substrate edge inspection systems.

In various embodiments according to this aspect of the invention, a quarter-wave plate is disposed between the light source and the beam deflector. In some embodiments a quarter-wave plate is disposed between the second flared parabolic surface and the detector. In some embodiments a Wollaston prism is disposed between the second flared parabolic surface and the detector. In some embodiments the detector is two detectors, where each detector has a different planar orientation. In some embodiments a scatter detector receives scattered light from the edge of the substrate. In some embodiments a beam expander is disposed between the light source and the beam deflector. In some embodiments a motor rotates the substrate.

According to another aspect of the invention, there is described an apparatus for inspecting an edge of a substrate while a motor rotates the substrate. A light source produces a light beam, and a beam expander receives the light beam and produces an expanded beam. A first quarter-wave plate receives the expanded beam and produces a circularly polarized beam. A two-dimensional beam deflector receives the circularly polarized beam and produces a semi-annular scanning beam. A first flared parabolic surface receives the semi-annular scanning beam and directs the semi-annular scanning beam onto the edge of the substrate while it rotates, thereby creating specularly reflected light and scattered light from the edge of the substrate. A second flared parabolic surface receives and directs the specularly reflected light, and a quarter-wave plate rotates the polarization of the specularly reflected light. A Wollaston prism receives the rotated specularly reflected light and produces a first specularly reflected light component and a second specularly reflected light component. A first detector receives the first specularly reflected light component and produces first signals, and a second detector receives the second specularly reflected light component and produces second signals. A scatter detector receives scattered light from the edge of the substrate while it rotates and produces third signals. An analyzer analyzes the first, second, and third signals and detects defects at the edge of the substrate.

According to yet another aspect of the invention, there is described a method for inspecting an edge of a substrate, by producing a light beam with a light source, receiving the light beam with a two-dimensional beam deflector, thereby producing a semi-annular scanning beam, receiving the semi-annular scanning beam with a first flared parabolic surface, directing the semi-annular scanning beam with the first flared parabolic surface onto the edge of the substrate, thereby creating specularly reflected light from the edge of the substrate, receiving the specularly reflected light with a second flared parabolic surface and directing the specularly reflected light to a detector, receiving the directed specularly reflected light with the detector, thereby producing signals with the detector, and analyzing the signals to detect defects at the edge of the substrate.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Various embodiments of an apparatus according to the present invention use a deflected focus beam to scan around the substrate edge, without physically moving an inspection head around the curvature of the substrate edge (from top to bottom), which increases the throughput of the inspection apparatus.

Figure 1:
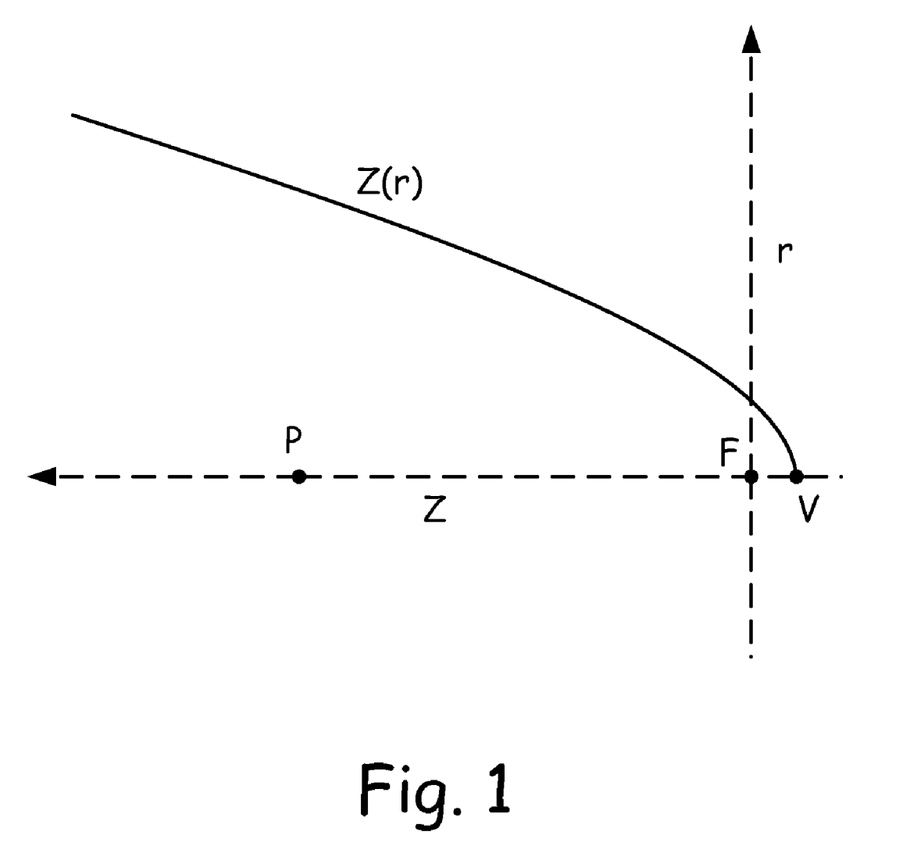
FIG. 1 depicts a parabolic curve with vertex V and focal point F.
Figure 2:
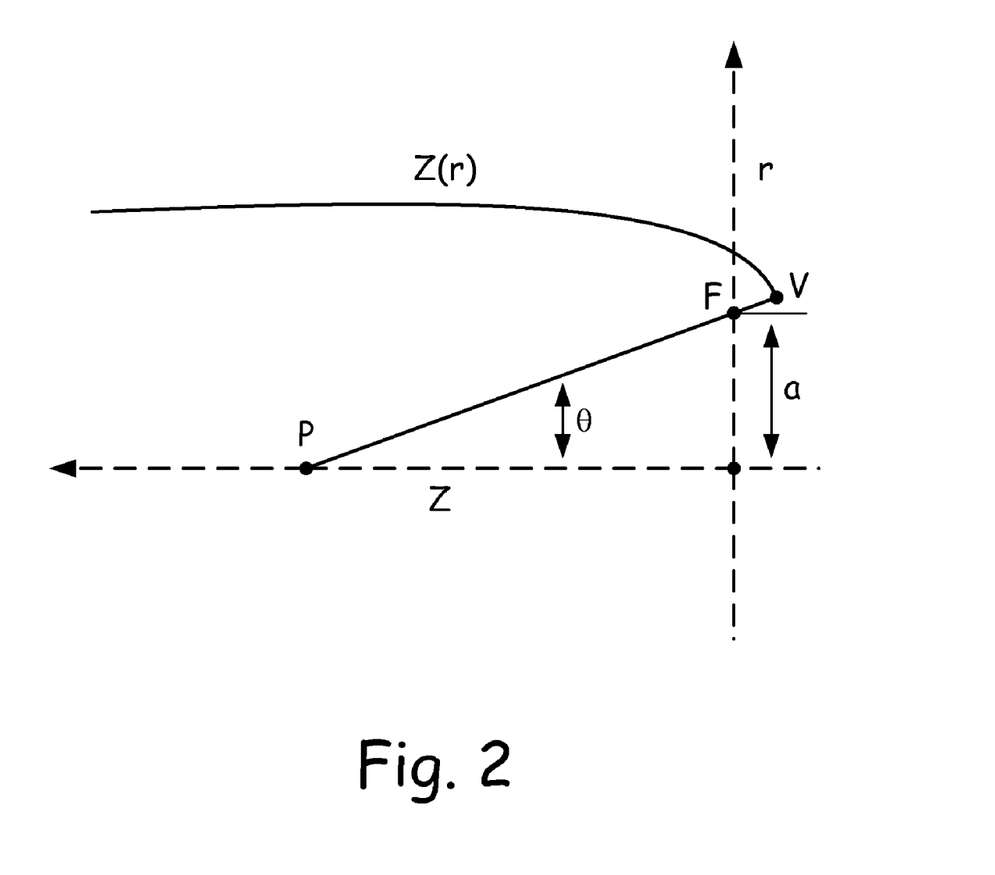
FIG. 2 depicts a tilted parabola about a pivot point P.

One component of the substrate edge inspection system is a flared parabolic reflector. The flared parabolic reflector is created as described below. The parabolic surface of the reflector is computed with an offset to bring the focal point to the origin, according to:

$$z(r) = c \cdot \frac{r^2}{2} - \frac{1}{2 \cdot c},$$

where $c = 1/R$, and R is the radius of curvature of the parabola at the vertex V FIG. 1 depicts a graphical representation of the vertex V and focal point F of a parabola according to the above equation. The parabola is then tilted around a pivot point P by an angle theta such that the focal point F is at a distance of a from the optical axis Z, as depicted in FIG. 2. The flared parabolic reflector surface shape is created with a revolution of about 180 degrees (about a half circle) of the tilted parabola of FIG. 2 around the optical axis Z.

Figure 3:
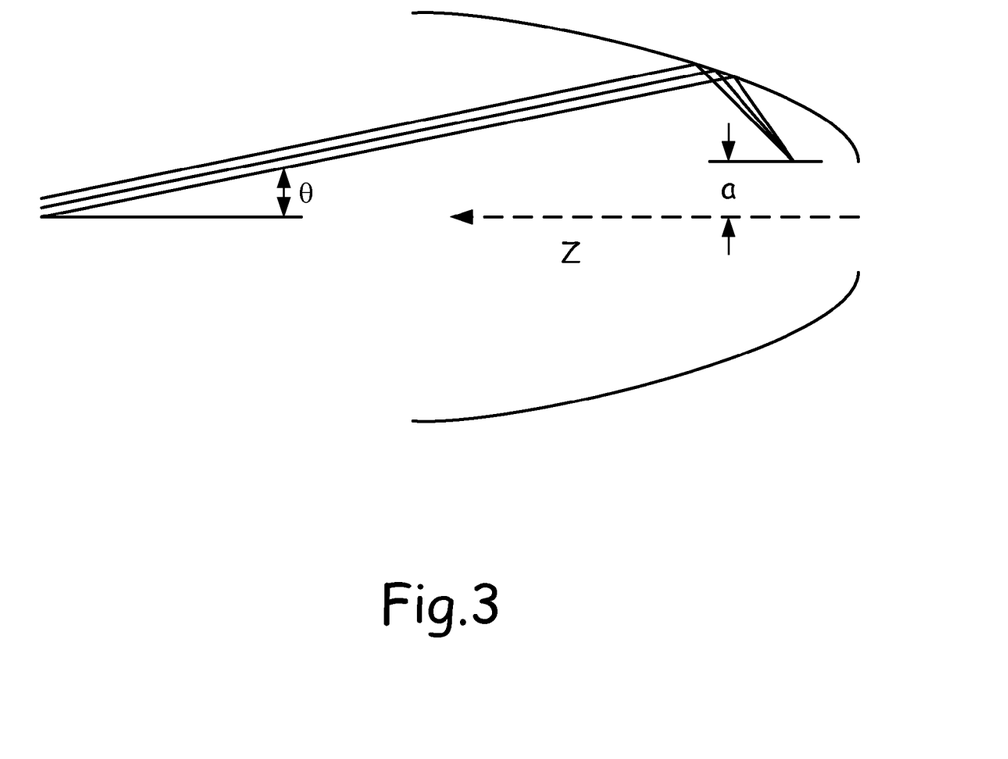
FIG. 3 depicts how a flared parabolic reflector brings a collimated beam with a field angle theta (with respect to optical axis Z) to a focal point that is offset by the distance a from the optical axis.
Figure 4:
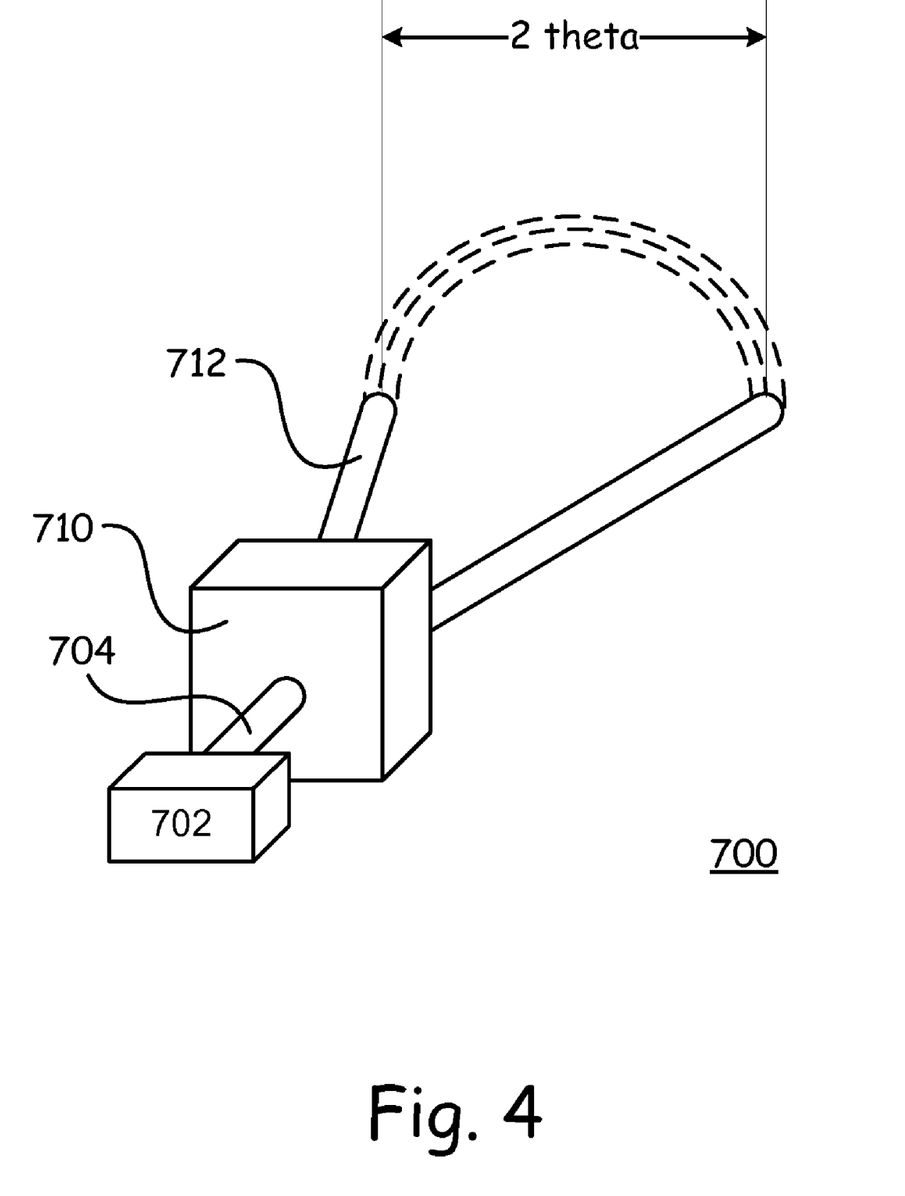
FIG. 4 depicts an acousto-optic deflector that is used to deflect a collimated beam about the optical axis by an angle 2*theta.

When a collimated beam with a field angle of theta with respect to the optical axis Z is incident on the inside surface of the flared parabolic reflector, it produces a focused spot that is offset by a distance a from the optical axis Z, as depicted in FIG. 3. The collimated beam 704, with a width of w, can be rastered with a two dimensional beam deflector 710 such as an acousto-optic deflector at the input of the flared parabolic reflector to produce an output beam with an approximate semi-annular scan around the optical axis Z, with a field angle of theta, into the input plane of the system 700, as depicted in FIG. 4.

Figure 5:
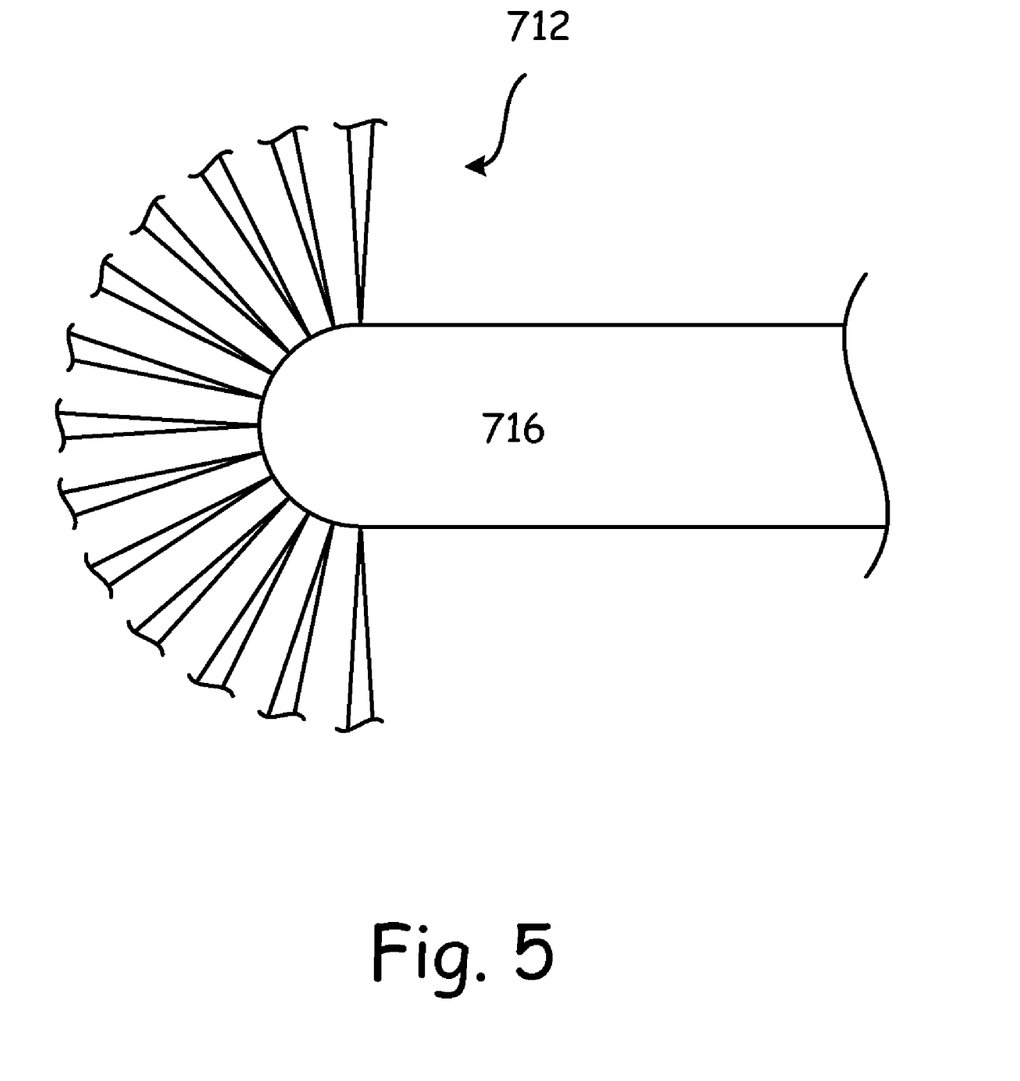
FIG. 5 depicts different views of the flared parabolic reflector with a deflected beam as input and a semi-annular focus on the substrate edge.

The approximately semi-annular scan from the flared parabolic reflector produces a focused spot path along the radial hemispherical edge of the substrate. FIG. 5 depicts how the flared parabolic reflector focuses the rastered beam 712 along the edge of the substrate 716.

Figure 6:
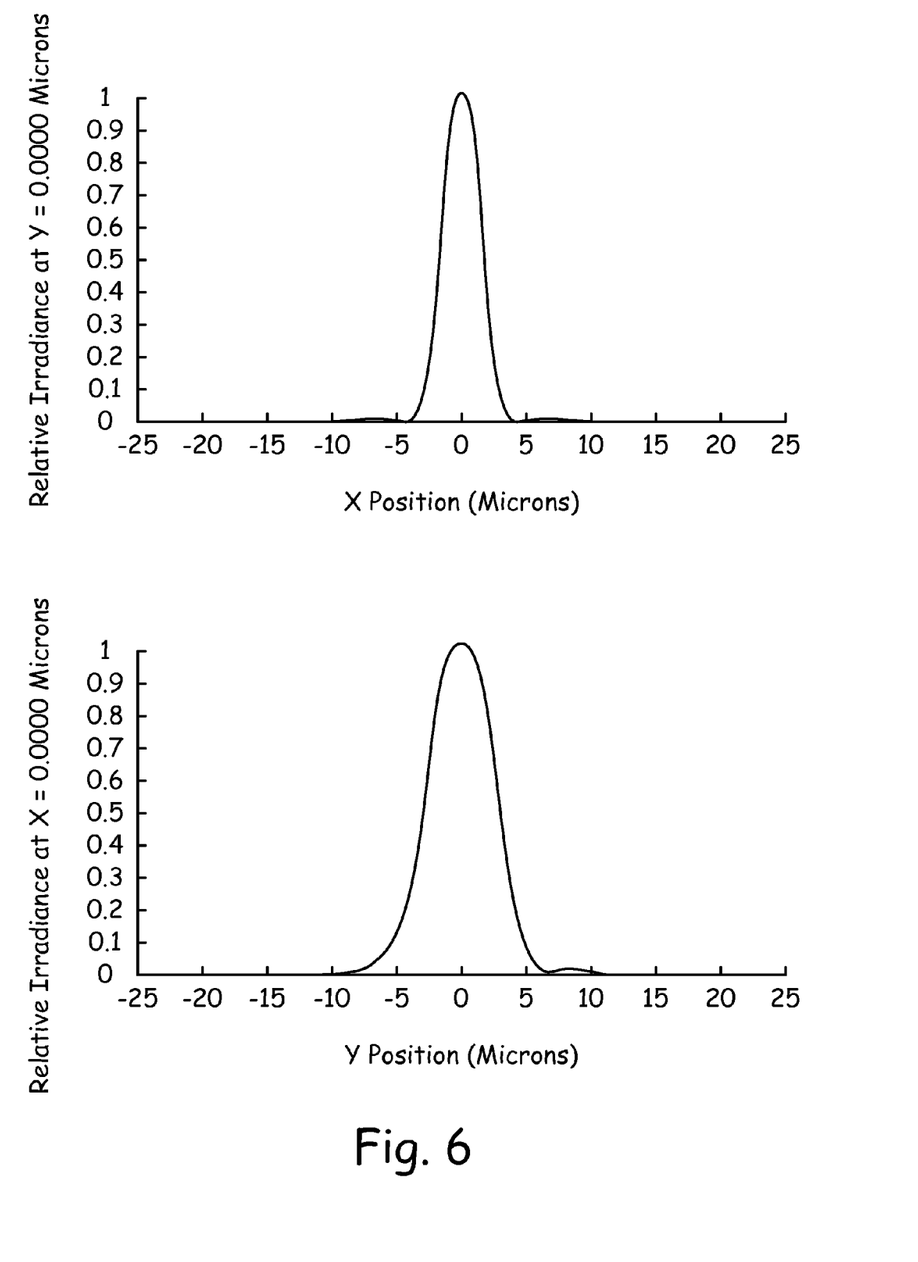
FIG. 6 depicts a Huygen point spread function cross-section in the X direction and the Y direction.

The spot size on the edge of the substrate 716 from the flared parabolic reflector as calculated using Huygens Point spread function is about 5.7 microns by about 9.6 microns along the substrate 716 edge. The Huygen point spread function cross-section is depicted in FIG. 6, depicting both the X cross section and the Y cross section.

Figure 7:
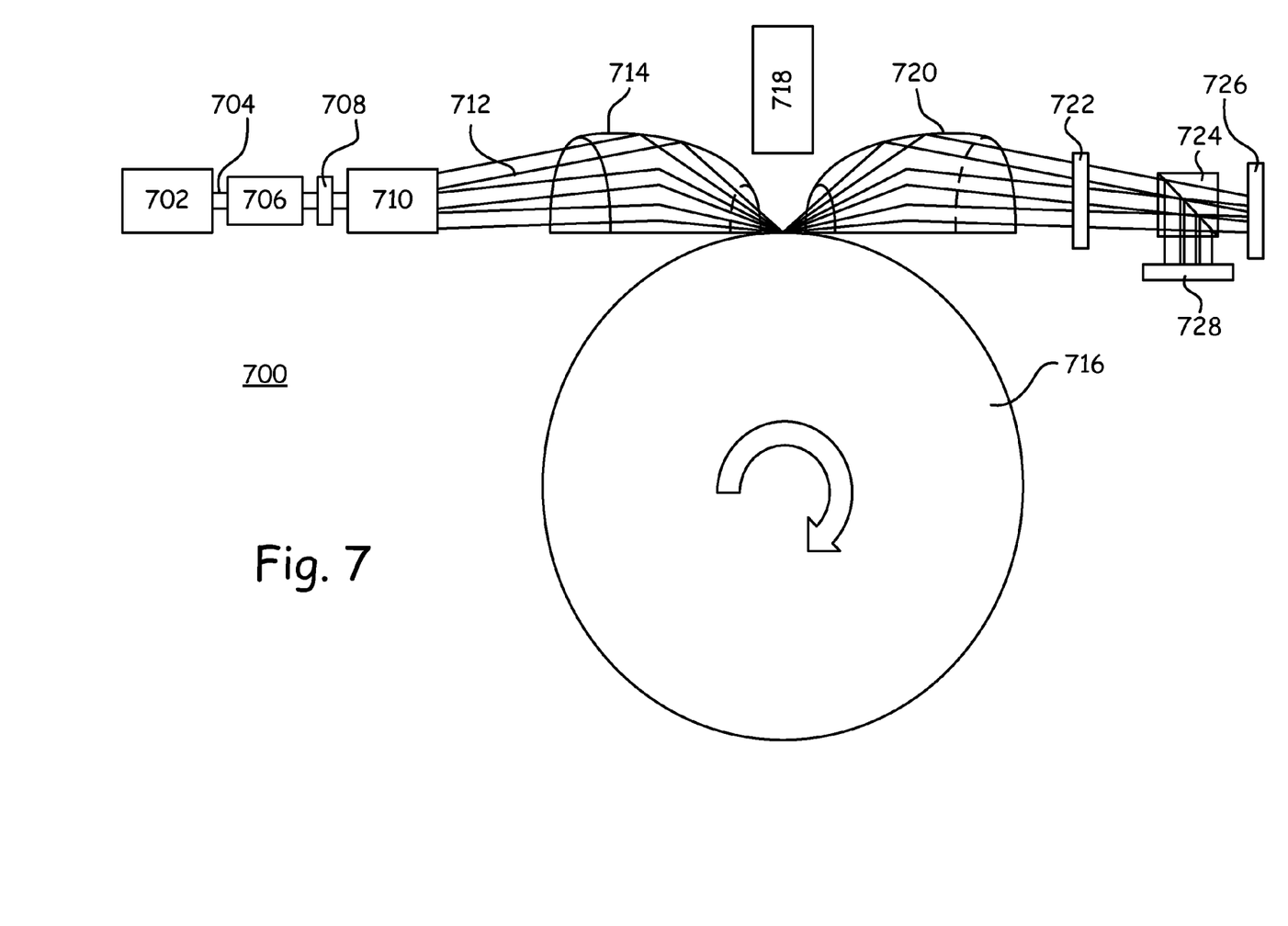
FIG. 7 depicts a functional block diagram of a substrate edge inspection system according to an embodiment of the present invention.

A functional representation of one embodiment 700 of an inspection system according to the present invention is depicted in FIG. 7. The depicted embodiment 700 uses a 405 nanometer, one hundred milliwatt laser 702 with a beam diameter of about 1.4 millimeters. The beam 704 is expanded to about four millimeters using a beam expander 706. In order to use a circular polarized beam 704, a first quarter-wave-plate 708 is disposed at an angle of about forty-five degrees to the orientation of polarization of the laser 702. The resultant beam 704 is input to a two-dimensional acousto-optic deflector 710 that creates a semi-annular scanning beam 712.

The scanning beam 712 is input to a first flared parabolic reflector 714, which produces a semi-circular focus on the substrate 716 edge (with detail as depicted in FIG. 5). The reflected beam 712 from the substrate 716 edge is directed to a second flared parabolic reflector 720, which collects the specularly reflected light and directs it through a second quarter wave plate 722 towards a Wollaston prism 724. The Wollaston prism 724 separates the different orientations of the polarization to determine the phases that might have been acquired due to reflections of the beam 712 off of defects on the substrate 716 edge. The two output beams from the Wollaston prism 724 are directed to two specular detectors 726 and 728. Any defects on the substrate 716 edge will reduce the amount of specularly reflected light, which the system 700 can determine.

Various embodiments according to the present invention can optically inspect the entire edge (from front to back) in a single rotation of the substrate 716. For example, when the acousto-optic deflector 710 is operated at about fifteen kilohertz and the spot size is about five microns, then the substrate 716 can be rotated one full revolution in about twelve seconds ($1/12$ Hertz). If twelve seconds is allowed for swapping substrates 716 into and out of the system 700 and processing the data that is generated by the scan, then this embodiment can inspect about one hundred and fifty substrates 716 an hour, which is many times faster than prior art systems. A scatter detector 718 can be added to the system 700 for additional edge analysis.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for inspecting an edge of a substrate, the apparatus comprising:
a light source for producing a light beam,
a two-dimensional beam deflector for receiving the light beam and creating a semi-annular scanning beam,
a first flared parabolic surface for receiving the semi-annular scanning beam and directing the semi-annular scanning beam onto the edge of the substrate, thereby creating specularly reflected light from the edge of the substrate,
a second flared parabolic surface for receiving and directing the specularly reflected light,
a detector for receiving the directed specularly reflected light and producing signals, and
an analyzer for analyzing the signals and detecting defects at the edge of the substrate.

2. The apparatus of claim 1, further comprising a quarter-wave plate disposed between the light source and the beam deflector.

3. The apparatus of claim 1, further comprising a quarter-wave plate disposed between the second flared parabolic surface and the detector.

4. The apparatus of claim 1, further comprising a Wollaston prism disposed between the second flared parabolic surface and the detector.

5. The apparatus of claim 1, wherein the detector further comprises two detectors, each detector having a different planar orientation.

6. The apparatus of claim 1, further comprising a scatter detector for receiving scattered light from the edge of the substrate.

7. The apparatus of claim 1, further comprising a beam expander disposed between the light source and the beam deflector.

8. The apparatus of claim 1, further comprising a motor for rotating the substrate.

9. The apparatus of claim 1, wherein the two dimensional beam deflector is a two dimensional acousto-optic beam deflector.

10. An apparatus for inspecting an edge of a substrate, the apparatus comprising:
   a motor for rotating the substrate,
   a light source for producing a light beam,
   a beam expander for receiving the light beam and producing an expanded beam,
   a first quarter-wave plate for receiving the expanded beam and producing a circularly polarized beam,
   a two-dimensional beam deflector for receiving the circularly polarized beam and producing a semi-annular scanning beam,
   a first flared parabolic surface for receiving the semi-annular scanning beam and directing the semi-annular scanning beam onto the edge of the substrate while it rotates, thereby creating specularly reflected light and scattered light from the edge of the substrate,
   a second flared parabolic surface for receiving and directing the specularly reflected light,
   a quarter-wave plate for adjusting the polarization of the specularly reflected light,
   a Wollaston prism for receiving the adjusted specularly reflected light and producing a first specularly reflected light component and a second specularly reflected light component,
   a first detector for receiving the first specularly reflected light component and producing first signals,
   a second detector for receiving the second specularly reflected light component and producing second signals,
   a scatter detector for receiving scattered light from the edge of the substrate while it rotates and producing third signals, and
   an analyzer for analyzing the first, second, and third signals and detecting defects at the edge of the substrate.

11. A method for inspecting an edge of a substrate, the method comprising the steps of:
   producing a light beam with a light source,
   receiving the light beam with a two-dimensional beam deflector, thereby producing a semi-annular scanning beam,
   receiving the semi-annular scanning beam with a first flared parabolic surface,
   directing the semi-annular scanning beam with the first flared parabolic surface onto the edge of the substrate, thereby creating specularly reflected light from the edge of the substrate,
   receiving the specularly reflected light with a second flared parabolic surface and directing the specularly reflected light to a detector,
   receiving the directed specularly reflected light with the detector, thereby producing signals with the detector, and
   analyzing the signals to detect defects at the edge of the substrate.

12. The method of claim 11, further comprising rotating the polarization of the light beam with a quarter-wave plate disposed between the light source and the beam deflector.

13. The method of claim 11, further comprising adjusting the polarization of the specularly reflected light with a quarter-wave plate disposed between the second flared parabolic surface and the detector.

14. The method of claim 11, further comprising splitting the specularly reflected light with a Wollaston prism disposed between the second flared parabolic surface and the detector.

15. The method of claim 14 further comprising receiving the specularly reflected light with two detectors, each detector having a different planar orientation.

16. The method of claim 11, further comprising receiving scattered light from the edge of the substrate with a scatter detector to produce signals.

17. The method of claim 11, further comprising expanding the light beam with a beam expander disposed between the light source and the beam deflector.

18. The method of claim 11, further comprising rotating the substrate with a motor.

19. The method of claim 11, wherein the two dimensional beam deflector is a two dimensional acousto-optic beam deflector.

20. The method of claim 10, wherein the two dimensional beam deflector is a two dimensional acousto-optic beam deflector.

* * * * *